(12) United States Patent
Brown et al.

(10) Patent No.: US 6,888,016 B2
(45) Date of Patent: May 3, 2005

(54) MIXTURES FOR STIMULATING GLUCOSE UP-TAKE

(75) Inventors: Anna Louise Brown, Sharnbrook (GB); Frederick William Cain, Wormerveer (GB); Ingrid Celestina Mohede, Wormerveer (GB); Preyesh Parmar, Sharnbrook (GB); Julia Sarah Rogers, Sharnbrook (GB); Ulrike Schmid, Wormerveer (DE)

(73) Assignee: Loders Croklaan USA LLC, Channahon, IL (US)

( * ) Notice: Subject to any disclaimer, the term of this patent is extended or adjusted under 35 U.S.C. 154(b) by 199 days.

(21) Appl. No.: 10/260,522

(22) Filed: Oct. 1, 2002

(65) Prior Publication Data

US 2003/0072785 A1 Apr. 17, 2003

(30) Foreign Application Priority Data

Oct. 16, 2001 (EP) .............................. 01308783

(51) Int. Cl.$^7$ .............................. C07C 57/00
(52) U.S. Cl. .................. 554/224; 554/227; 514/546; 514/547; 514/552; 514/560; 514/866; 424/195.11; 424/439; 424/451
(58) Field of Search ................ 554/224, 227; 514/546, 547, 552, 560, 866; 424/195.11, 439, 451

(56) References Cited

U.S. PATENT DOCUMENTS

2002/0081315 A1 * 6/2002 Katz et al. ............. 424/195.16

FOREIGN PATENT DOCUMENTS

WO        99/29317        6/1999

* cited by examiner

Primary Examiner—Deborah Carr
(74) Attorney, Agent, or Firm—Morgan, Lewis & Bockius LLP

(57) ABSTRACT

Our invention concerns a mixture of CLA glycerides, and/or CLA-fatty acids and or CLA-alkyl esters and another component, wherein the other component (=component A) is selected for its capacity to alleviate problems related to insulin resistance in mammals, using CLA rich diets and/or foods and/or food supplements using an appropriate in vitro test so that in at least one step of the in vitro test, as described in the text, an improvement in test results is obtained of at least 4% by the blend of the CLA derivative and component A when compared to the CLA derivative only.

Figure 1:
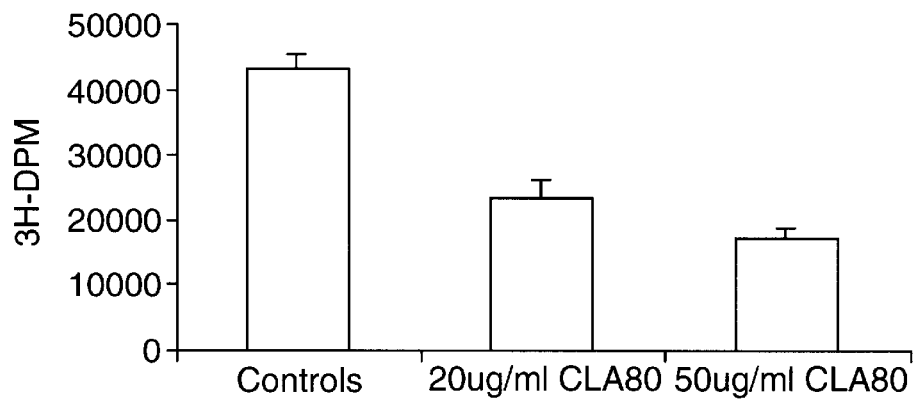

The inventon further concerns CLA rich dietic food, food supplements and foods containing the combination of CLA and component A as defined, while also the use of this combination for achieving an alleviation of insulin resistance is part of the invention.

20 Claims, 1 Drawing Sheet

MIXTURES FOR STIMULATING GLUCOSE UP-TAKE

Conjugated linoleic acid (=CLA) and derivatives such as glycerides or alkyl esters or inorganic salts thereof are well known for a number of health effects. According to WO 99/29317 CLA can be used to treat diabetes by administering an effective amount of CLA to a human suffering from diabetes. The administration of CLA results in a modulation of the level of expression of certain genes involved in the regulation of lipid and glucose metabolism enzymes and/or in the regulation of adipocyte differentiation. It is concluded in this document that the administration of CLA can normalize glucose tolerance and reduce plasma insulin, triglyceride and free fatty acid levels. The CLA can be administered in any suitable form including powders or as mixtures with oils. The CLA also may contain antioxidants or free fatty acids.

We found that although CLA might affect the expression of genes as disclosed in WO 317 it can also reduce insulin stimulated glucose up-take by adipocytes from mammals. A reduction in insulin stimulated glucose uptake is a characteristic of insulin resistance. This reduction in insulin stimulated glucose up-take is an important property to address, because this property plays an essential role in the way the persons consuming the CLA may react to the intake of CLA. Therefore we tried in our study to find ways that could be used to stimulate the glucose up-take by adipocytes from mammals. This study resulted in the finding of novel mixtures that can be used for this purpose.

Therefore our invention concerns in the first instance a mixture of CLA glycerides, and/or CLA-fatty acids and or CLA-alkyl esters and/or salts and another component, wherein the other component (=component A) is selected for its capacity to stimulate glucose up-take in adipocytes from mammals, using an appropriate in vitro glucose up-take assay wherein the glucose up-take stimulation is at least 4%, preferably at least 20% better by use of the blend of the CLA derivative and component A when compared to the use of the CLA or CLA derivative only.

Test Protocol
1. Evaluation of Glucose Uptake in Adipocytes
Differentiation of Adipocytes Murine (3T3-L1 cells; ATCC CL-173) were seeded into multi-well plates and incubated in growth medium (DMEM supplemented with 10% FCS, 2 mM L-glutamine, 100 iu/ml penicillin and 100 $\mu$g/ml streptomycin) at 37° C./5% CO2 until 2 days post-confluence (day 0). Differentiation was carried out approximately according to Iwata et al (Diabetes 2001 50: 1083–1092). Briefly, differentiation was induced by changing to growth medium containing 3-isobutyl-1-methylxanthine (0.5 mM), dexamethasone (0.25 $\mu$M) and 1 $\mu$M insulin for 3 days, and then growth medium containing 0.8 $\mu$M insulin for another 3 days. Finally cells were retained in serum free growth medium until ready for experimentation, typically cells were used between days 6–9.

Preparation of Samples.

Pine nut oil (PNO) and palm kernel oil (PKO) fatty acids were prepared by saponification of pine nut oil or palm kernel oil. PNO contains high levels of PUFAs, in particular high levels of pinolenic acid. PKO has high levels of medium chain fatty acids (C8–12). All samples were prepared as 1 mg/ml stocks in ethanol and diluted in media accordingly with the following exceptions. IGF-1 was prepared by initially dissolving in 100 10 mM HCl, followed by the addition of 400 $\mu$l PBS supplemented with 1 mg/ml BSA. This was diluted with media to the correct concentration. Ascorbic acid, sodium vanadate and aspartame were made up in DMEM.

Evaluation of Glucose Uptake

Differentiated adipocytes were incubated for a period of 3 days in DMEM (containing 2 mM L-glutamine, 100 iu/ml penicillin, 100 $\mu$g/ml streptomycin, 1 nM insulin and 10% FCS) supplemented with or without CLA and/or compound As. The cells were then washed three times with DMEM (containing 1 mM deoxyglucose). Insulin stimulated glucose uptake was carried out according to Iwata et al (Diabetes 2001 50: 1083–1092). Briefly, cells were stimulated with 1 nM insulin in Krebs Ringer Phosphate (KRP) and HEPES buffer [10 mM HEPES, 131.2 mM NaCl, 4.7 mM KCl, 2.5 mM $CaCl_2$, 1.2 mM $MgSO_{4,\ 2.5}$ mM sodium phosphate buffer, pH 7.4] with 1% BSA at 37° C. After 1–30 minutes the assay was initiated by addition of 10 $\mu$l KRP containing 2.5 $\mu$Ci [$^3$H]2deoxyglucose and 1 mM deoxyglucose. After 1 hr the reaction was terminated by washing the cells 3× with ice-cold DMEM. Cells were then solubilised with 500 $\mu$l/well of 1% Triton X-100, 0.2% SDS and 0.2N NaOH for 20 minutes at 37° C. Radioactive incorporation was measured by scintillation counting of 100 $\mu$l of each cell lysate.

The data illustrating the effects of CLA alone on glucose uptake is represented by the radiolabel incorporation (3H-DPM) during the experiment. The data showing the effects of compound A's in combination with CLA is represented as a percentage of the CLA treatment alone. So any value above 100% demonstrates an increase in glucose uptake over CLA alone. (of FIGS. 1 and 2).

Typical examples of components A that were found as suitable are components selected from the group consisting of pine nut oil, palm kernel oil, ascorbic acid and salt and ester derivatives thereof (in particular Na and K salts and fatty acid esters, monoglycerides e.g. monoolein, vanadium salts e.g. sodium vanadate, phospholipids e.g. lecithin, sweeteners e.g. aspartame, phytoestrogen containing extracts e.g. Soylife, containing isoflavones.

An additional compound A could be IGF-1, purified or in natural extracts e.g. new zealand deer antler, or compounds or extracts known to boost IGF-1 in vivo e.g. DHEA, essential amino acids such as arginine, lysine and ornithine, or colostrum, milk, calcium, cowpea, lupin, zinc supplements.

Additional benefits may also be found from combinations of >1 compound A in combination with CLA.

The mixtures according to the invention preferably comprise the CLA derivative and component A in weight ratios of CLA-derivative (calculated as free CLA) to component A of 1:99 to 99:1, preferably 80:20 to 20 to 80 most preferably 30 to 70 to 70 to 30.

CLA can comprise about 8 different isomeric isomers (cis/trans isomers). It was found that from these isomers the trans10 cis9 isomers are the most effective for use in dietic food and therefore we prefer to use as CLA glycerides and/or the CLA fatty acids and/or the CLA alkyl esters those derivatives that are rich in the trans10 cis12CLA isomer, preferably having more than 30 wt % trans10cis12-CLA, more preferably more than 50 wt % trans10cis12-CLA and in particular more than 70 wt % of the trans10cis12-CLA isomer.

The mixtures as defined above can be used as such but often it is advantageous to use them as blend with another component. Preferred other components are fats and therefore we prefer to apply a blend of one or more vegetable fat(s) and at least 3 wt %, preferably 5 to 35 wt %, most preferably 7 to 25 wt % of the mixtures according to the invention. In order to obtain good mouthfeel we prefer to use a blend, wherein the total fat phase displays a solid fat content measured on a non-stabilised fat by NMR-pulse at the temperature indicated of: 5 to 90 at 5° C.; 2 to 80 at 20° C. and less than 15 at 35° C. Non stabilised meaning that the fat after being melted at 80° C. was cooled to 0° C. and kept at 0° C. for 30 min, after which the fat is heated to measurement temperature and kept thereon for another 30 min whereupon its solid fat content was measured by NMR-pulse The mixtures and blends as defined above can be used in CLA rich diet food wherein the diet food comprises a food or drink component, 1 or more component As, capable of stimulating glucose up-take in adipocytes from mammals and wherein component A is present in amounts corresponding with a daily intake of 1 mg to 10 grams of component A per day.

It is also possible to use our mixtures or blends in encapsulated food supplements. Hereto encapsulated products are made that comprise an effective amount of the mixture according to the invention in encapsulated form whereby the encapsulating material preferably is selected from the group consisting of starch materials, modified starch materials, gelatin, sugars, gums, hydrocolloids The CLA and component A containing mixtures or blends can also be used in food products. These food products will comprise the mixture or the blend according to the invention.

Typical foods can be selected from the group consisting of spreads (low fat or full fat), dressings, mayonnaises, cheese, creams, ice creams, ice cream coatings, confectionery coatings, fillings, sauces, culinary products and baked goods, bars, drinks, soups, dairy based drinks, powders and health drinks.

According to another embodiment our invention also comprises the use of a mixture of CLA glycerides, and/or CLA-fatty acids and or CLA-alkyl esters and other components, (=component A) according to the invention for the production of a food or a food supplement with the ability to stimulate glucose up-take in the adipocytes from mammals.

More specifically our invention also concerns the use of a CLA rich diet food wherein the diet food comprises conventional food components, 1 or more component A's and CLA in amounts corresponding with a daily intake of at least 2 g CLA per day, preferably at least 5 g per day most preferably 6 to 10 g per day and wherein the diet food is used to stimulate the glucose up-take by adipocytes from mammals.

More preferably our invention concerns the use of the mixtures or blends wherein the blend comprises one or more vegetable fat (s) and at least 3 wt %, preferably 5 to 35 wt %, most preferably 7 to 25 wt % of the mixtures according to the invention.

The food product produced in particular is a food product selected from the group consisting of spreads (low fat or full fat), dressings, mayonnaise, cheese, creams, ice creams, ice cream coatings, confectionery coatings, fillings, sauces, culinary products and baked goods According to a last embodiment our invention also concerns a method of stimulating the glucose up-take by adipocytes from mammals by administering the mammals an effective daily amount of a mixture according to the invention or a blend according to the invention.

Effective amount in this patent application being defined as that amount that gives a noticable effect. This amount might be different for the different compositions and even for the different humans consuming the compositions but this amount can be determined easily by the man skilled in the art.

EXAMPLES

Example 1

The Effects of CLA on Insulin Stimulated Glucose Uptake in 3T3-L1 Adipocytes

The insulin stimulated glucose uptake (ISGU) of control differentiated adipocytes were compared with those treated with CLA fatty acids (50:50 ratio of the main isomers, should we include here CLA A80?) at a concentration of 10 or 50 $\mu$g/ml. As shown in FIG. 1, CLA reduces ISGU compared with the control.

Example 2

Effects of Compound A's on ISGU in Adipocytes

Figure 2:
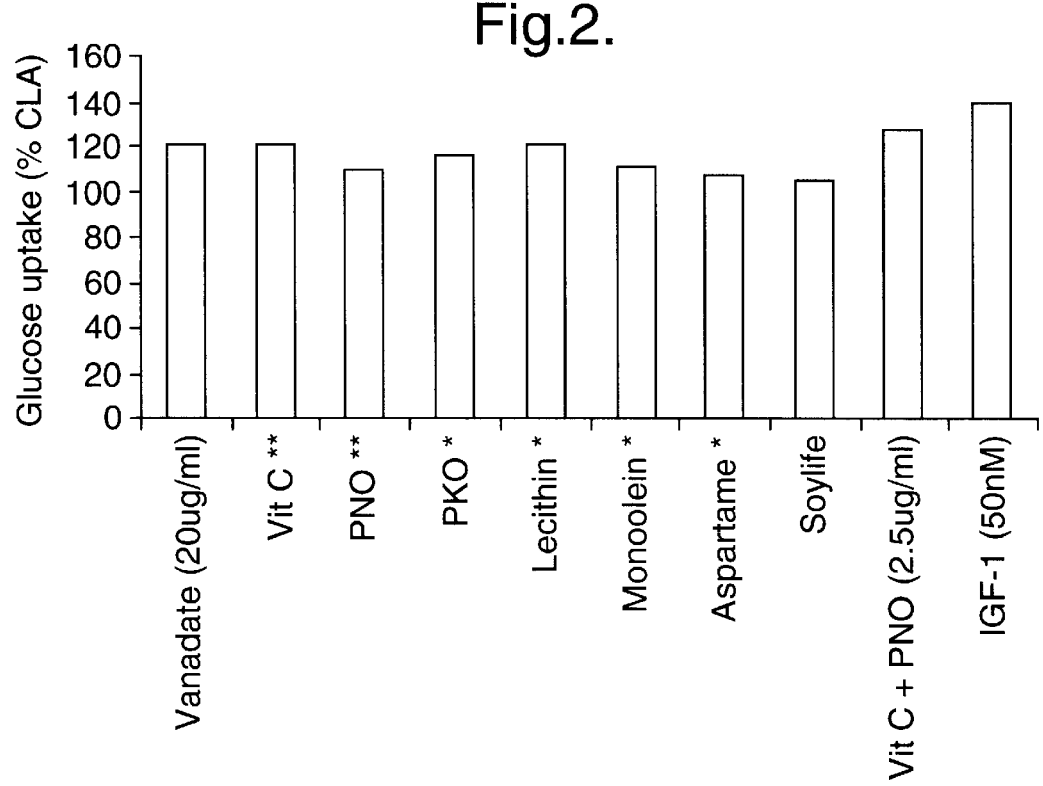

As shown in FIG. 2, a number of compound A's boosts glucose uptake above CLA alone. The increase in glucose uptake in combination with CLA by Vit C (20%), PNO (21%), vit C+PNO (27%) and IGF-1 (39%) in particular were significantly higher than CLA alone. P<0.05 as determined using a Students T-test.

What is claimed is:

1. A mixture of at least one CLA component selected from the group consisting of CLA glycerides, CLA-fatty acids and CLA-alkyl esters, and another one or more components A, wherein said CLA component is such that it can reduce insulin stimulated glucose uptake by adipocytes and wherein component A is selected for its capacity to stimulate glucose up-take in adipocytes from mammals, using an appropriate in vitro glucose up-take assay whereby the glucose up-take stimulation is at least 4% better by use of the mixture of the CLA component and component A when compared to the use of the CLA component only.

2. Mixture according to claim 1 wherein component A is selected from at least one member of the group consisting of pine nut oil acids or esters, pinolenic acid or esters, palm kernel acids or esters, ascorbic acid and the salt and ester derivatives thereof, vanadiurium salts, lecithin, monoglycerides, aspartame, soy extracts, IGF-1 or IGF-1 boosting agents.

3. Mixture according to claim 1 or 2 wherein the weight ratio of CLA component (calculated as free CLA) to component A is 1:99 to 99:1.

4. Mixture according to claim 1 wherein the CLA glycerides, CLA fatty acids and CLA alkyl esters are rich in the trans10cis 12-CLA isomer.

5. A blend of one or more vegetable fat(s) and at least 3 wt % of a mixture according to claim 1.

6. Blend according to claim 5 wherein the total fat phase displays a solid fat content measured on a non-stabilised fat by NMR-pulse at the temperature indicated of: 5 to 90 at 5° C. to 80 at 20° C. and less than 15 at 35° C.

7. A CLA rich diet food wherein the diet food comprises a food component, a component A, capable of stimulating glucose up-take in adipocytes from mammals and wherein component A is present in amounts corresponding with a daily intake of 1 mg to 10 grams of component A per day.

8. Food supplement comprising an effective amount of the mixture according to claim 1 in encapsulated form, whereby the encapsulating material is selected from the group consisting of starch materials, modified starch materials, gelatine, sugars, gum, hydrocolloids.

9. Food products comprising a mixture according to claim 1 or blend according to claim 5.

10. Food products according to claim 9, wherein the food product is selected from the group consisting of spreads (low fat or full fat), dressings, mayonnaise, cheese, creams, ice creams, ice cream coatings, confectionery coatings, fillings, sauces, culinary products, backed goods, bars, drinks, soups, dairy based drinks, powders and health drinks.

11. The method of producing a food or food supplement with the ability to stimulate glucose up-take in the adipocytes of mammals which comprises adding to said food or food supplement, an effective amount of a mixture according to claim 1 or blend of claim 5.

12. The method of stimulating the glucose up-take in adipocytes of mammals which comprises administering thereto a CLA rich diet food according to claim 7.

13. The method of stimulating the glucose up-take in adipocytes of mammals which comprises administering to said mammals an effective daily amount of a mixture according to claim 1 or blend according to claim 5.

14. The method of claim 13 wherein the blend comprises at least one vegetable fat and at least 3 wt % of said mixture.

15. The method of claim 11 wherein the food is selected from the group consisting of low fat or full fat spreads, dressings, mayonnaises, cheese, creams, ice creams, ice cream coatings, confectionery coatings, fillings, sauces, culinary products and baked goods, bars, drinks, soups, dairy-based drinks, powders and health drinks.

16. The mixture of claim 1 wherein the glucose up-take stimulation of said mixture is at least 20% better when compared to the use of the CLA component alone.

17. The mixture of claim 3 wherein the weight ratio of CLA component to component A is 30 to 70 to 70 to 30.

18. The mixture of claim 4 wherein at least one of the CLA glycerides, CLA fatty acids and CLA alkyl esters has more than 30 wt % trans10cis 12-CLA.

19. The mixture of claim 4 wherein at least one of the CLA glycerides, CLA fatty acids and CLA alkyl esters has more than 70 wt % trans10cis 12-CLA.

20. The blend of claim 5 containing 7 to 25 wt % of said mixture.

* * * * *